(12) United States Patent
Gunawardena et al.

(10) Patent No.: US 7,779,025 B2
(45) Date of Patent: Aug. 17, 2010

(54) SYSTEM AND METHOD FOR EVALUATING DATA SETS OVER A COMMUNICATIONS NETWORK

(75) Inventors: Jamila Gunawardena, Palo Alto, CA (US); Jacques Reifman, New Market, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 379 days.

(21) Appl. No.: 11/298,606

(22) Filed: Dec. 12, 2005

(65) Prior Publication Data

US 2006/0202037 A1 Sep. 14, 2006

(51) Int. Cl.
*G06F 7/00* (2006.01)
(52) U.S. Cl. .................. 707/766; 707/769; 600/300
(58) Field of Classification Search .......... 707/10, 707/1, 3, 999.001, 999.003, 999.01, 766, 707/769; 600/300
See application file for complete search history.

(56) References Cited

U.S. PATENT DOCUMENTS

| | | | | |
|---|---|---|---|---|
| 6,383,136 B1 * | 5/2002 | Jordan | .................. | 600/300 |
| 6,405,195 B1 | 6/2002 | Ahlberg | | |
| 6,611,822 B1 | 8/2003 | Beams et al. | | |
| 6,615,253 B1 | 9/2003 | Bowman-Amuah | | |
| 6,901,428 B1 | 5/2005 | Frazier et al. | | |
| 7,089,236 B1 | 8/2006 | Stibel | | |
| 2002/0007285 A1 * | 1/2002 | Rappaport | .................. | 705/2 |
| 2002/0029236 A1 * | 3/2002 | Burgel et al. | .................. | 709/1 |
| 2002/0082825 A1 * | 6/2002 | Rowlandson et al. | .......... | 704/9 |
| 2003/0125632 A1 * | 7/2003 | Takizawa | .................. | 600/509 |
| 2004/0148291 A1 | 7/2004 | Dorsett, Jr. | | |
| 2005/0204041 A1 * | 9/2005 | Blinn et al. | .................. | 709/225 |
| 2005/0222928 A1 * | 10/2005 | Steier et al. | .................. | 705/35 |
| 2006/0040711 A1 * | 2/2006 | Whistler | .................. | 455/566 |

OTHER PUBLICATIONS

International Searching Authority, International Search Report and Written Opinion issued Jan. 31, 2007, with respect to International Application No. PCT/US05/45005 filed on Dec. 13, 2005.

* cited by examiner

*Primary Examiner*—Khanh B Pham
*Assistant Examiner*—Amy Ng
(74) *Attorney, Agent, or Firm*—Elizabeth Arwine (57) ABSTRACT

The present invention is directed to a system and method for providing researchers with a computer-assisted tool to evaluate, over a communications network, large electronic data sets stored on a remote server. The system allows the centralization of multiple data manipulation and analysis software modules co-located with the large data sets to reduce the amount of data from the data sets and software that has to be downloaded to a particular user's client computer. The system is designed to accommodate multiple researchers located at different geographic locations each of whom may have, with regard to the data, different scientific research objectives.

37 Claims, 2 Drawing Sheets

SYSTEM AND METHOD FOR EVALUATING DATA SETS OVER A COMMUNICATIONS NETWORK

BACKGROUND OF THE INVENTION

1. Field of Invention

The present invention relates to computer-implemented data management and analysis systems and methods. In particular, the present invention is related to a system and method for warehousing, managing, and analyzing large time-series and non time-series data files stored on a server by collaborative researchers who are located at remote locations but who are in data communication with the server.

2. Description of the Related Art

Collaboration among research scientists using distributed client computers over a communication network is not new. For example, U.S. Pat. No. 6,611,822 describes a collaborative session that involves establishing a network connection between a plurality of users, selecting a mode for the network connection between the plurality of users, establishing a network connection mode between the plurality of users, and synchronizing the mode between the plurality of users. The patent teaches that the modes of operation include application and information sharing over the network.

Often, collaborative research involves analyzing data sets. U.S. Pat. No. 6,615,253 describes a system involving server side data retrieval for execution of client side applications. The patent teaches a method of requesting data stored on a server over a network, bundling the data into a data structure in response to the request, and sending the data structure to a client computer over the network, whereby the data structure is cached on the client and used as needed during execution of the application running on the client.

Client applications for analyzing data have been around for may years. One of the more robust applications, MATLAB®, provides a "distributed computing toolbox" and a "distributed computing engine" that enable users to develop distributed analysis applications and execute them over a cluster of different computers (presumably even ones geographically remote from each other) without leaving a central development environment where the user is located. The data set, or a portion thereof, must still reside on each of the distributed computers, and the analysis module inputs for data mining are created from scratch by the user.

Similarly, simple spreadsheet programs like Microsoft® Excel® can be used to store, in a file on a client computer, a set of data records that can be shared by multiple users over a network so that collaborators can each manipulate the data for his or her use. However, this requires each collaborator to develop data mining queries, conduct mathematical operations, and analyze the results on his or her own computer.

While the aforementioned data analysis and collaboration techniques, and others like them, are feasible for relatively small data sets, the method is not suitable for very large data sets, especially time-series data sets that can easily range between tens to hundreds of gigabytes of data and require the collaboration of domain experts in diverse fields engaged in the research process. Traditionally, as taught by the above patents, the data sets need to be electronically distributed to the collaborators so they can analyze them using analytical applications running on their own computers. Thus, each research team had to locally maintain the tools necessary to properly handle and store the data. Moreover, facilities for querying and analyzing the data would need to have been developed by each researcher using the application on his or her client compute. Furthermore, establishing common facilities among the various collaborative groups and overcoming issues of hardware and software incompatibility would need to have been addressed. Also, the lack of an integrated system for managing and analyzing large sets of time-series data forced collaborators to develop endless data input-output interface systems for sequential data analysis.

U.S. Pat. No. 6,405,195 addresses some of those problems. It describes a system in which data to be analyzed is transferred from one or more user systems to a host system, which includes an analysis/decision support module. Queries are generated, either automatically by the analysis/decision support module, or by the user, who then submits them to the host system. As taught in the patent, more than one user may participate in the system, including transferring data to the host. This joint participation includes the option of collaboratively submitting or adjusting queries and viewing the results of the data analysis, either in real time, or asynchronously. Data used as the basis of an analysis may therefore come from different entities, even from databases that are available publicly via the network, but whose owners are not participants in the collaborative, hosted analysis system according to the disclosed invention. The patent also describes how the host system acts as a network portal through which different users may store and share not only data for analysis, but also the results of such analysis. Notwithstanding the above, the patent does not deal with very large time-series data records, which present unique challenges over conventional database management systems.

Existing database management systems are not optimal for the management of very large time series data, since they were not built with this objective. Their storage architecture is not structured to effectively handle ordered data and simple time series operations are poorly supported. Querying the data requires writing statements in some form of query language; this is acceptable in business applications where the same queries are performed over and over again, but becomes burdensome when the database must be subjected to ad hoc queries. The burden, then, on collaborative researchers has traditionally been placed on the research team itself to construct a solution from scratch, resulting in each research study requiring its own effort to combine data storage, search, and analysis in order to reach certain research objectives.

Accordingly, there exists the need for a system and method for evaluating data over a communications network that is an efficient and effective collaboration tool for remote researchers. The present invention allows researchers to transition away from the mundane yet necessary task of data and system management that has plagued the prior art systems and methods of time-series data evaluation, and to focus on their core research objectives: data mining and analysis.

SUMMARY AND OBJECTS OF THE INVENTION

The Combat Casualty Care Directorate of the U.S. Army Medical Research and Materiel Command (USAMRMC), Ft. Detrick, Md., supports various intramural and extramural research studies involving the collection and analysis of human and animal physiological data. Those studies generate voluminous amounts of time-series data, such as, but not limited to, electrocardiogram waveforms (EKG), oxygen saturation waveform (SpO2), and respiratory traces, that traditional relational database management systems are ill-suited to handle. Therefore, those data sets are generally stored by investigators in their individual workstations and are manually manipulated for subsequent visualization and analysis.

To afford a flexible solution to warehouse and manage physiologic data sets and provide analytical tools to research scientists for post-hoc analysis of time-series data in a central location, the USAMRMC Bioinformatics Cell has developed the present invention. The present invention is directed to a system and method designed to support the disparate needs of storing and mining data from various studies conducted by various researchers located at different geographical locations. The system can be used, for example, to warehouse and analyze continuous pre-hospital physiologic vital sign data collected from trauma patients during transport from a scene of an incident to a trauma center.

The present invention is designed to, among other things: (1) permit the integration of data management and data analysis into a single, central integrated computer system; (2) eliminate the need for users to download large amounts of time-series data from a data storage device into the user's workstation for subsequent data analysis; (3) eliminate the need for the users to download and maintain data analysis tools in their workstation; (4) permit the user to easily customize his/her own sequence of data analysis operations; (5) allow the user to query across different studies, with the ability to interrogate both time-series and non-time-series data; (6) permit the user to visualize the original or operated upon time series data; (7) permit the storage on the server of user-performed operations for future access; and (8) facilitate on-line collaboration among different research groups and domain experts.

Accordingly, it is principal object of the present invention to provide a system and method for providing researchers with a computer-assisted tool to evaluate, over a communications network, large electronic data sets stored on a remote server, whereby the system allows the centralization of multiple data manipulation and analysis software modules co-located with the large data sets to reduce the amount of data from the data sets and software that has to be downloaded to a particular user's client computer.

It is still another object of the present invention to provide a system and method for data evaluation that can identify physiologic parameters that are early indicators of some clinical outcome, such as a need for a life saving intervention (LSI), leading to usable triage algorithms that help first responders identify the immediate need for casualty evacuation or immediate care.

It is another object of the invention to provide a computer system for warehousing, managing, visualizing and analyzing time-series data.

It is still another object of the invention to provide a system and method for data evaluation that is flexible, interactive, and easy-to-use.

It is another object of the invention to provide a system and method designed for researchers for post-hoc analysis of studies involving time-series data.

It is still another object of the invention to provide a system and method that offers, through a Web browser, a feature-rich, workstation-like environment to perform sophisticated data mining by integrating both data and analysis tools at a central server location, and thereby allowing researchers to manipulate and mine large amounts of time-series data at the server, eliminating the need to download information to the researcher's workstation.

The key advantage of the subject invention is the integration of data management and data analysis capabilities for large sets of time-series data into a single system, eliminating the need for downloads to the user's desktop. The invention allows the user to, among other things: (1) store data sets into the system; (2) query the system and retrieve specific data subsets of interest that meet user-defined criteria; (3) visualize time-series data; (4) perform univariate and multivariate data analysis through a series of user-specified and user-constructed analysis functions; and (5) export data.

Existing systems allow either the management of time-series data or analysis of time-series data, but not both. In addition, the present invention allows the user to customize data analysis. This is accomplished by providing a flexible mechanism for users to provide their own analysis tools to the system's library of functions and an interactive mechanism for users to construct sequential analysis operations. Furthermore, any operation performed by the user, such as data query and data analysis, is stored in the system for future reference and subsequent analysis.

Thus, the invention is useful to research organizations involved in the collection and analysis of continuous physiologic data. Moreover, the system is equally useful to analysis of time-series data encountered in industrial processes, such as nuclear and fossil power plants and chemical plants, monitoring of critical systems, such as aircrafts and space shuttles, and financial markets. The system is useful for both experienced and inexperienced data miners, as it allows for the creation and storage of analysis functions for repetitive usage and, through its modular and flexible architecture, the easy incorporation of user-developed and third-party analysis tools.

Briefly described, the apparatus aspect of the invention includes system architecture where both the data and the analysis tools reside at the server while offering—through a Web browser—a feature-rich, workstation-like environment that researchers require to perform sophisticated data mining. Timely system performance is provided by efficiently splitting the processing of non-time-series data and time-series data between the Relational Database Management System and the Binary Flat File configuration, respectively. User interaction is segmented into three distinct and yet integrated components, Query, Functions, and Analysis, which are separately and independently customized by the user, but integrated by an automatic tracking system that keeps track of the sequence of operations performed in a given computer session. The system allows for easy and rapid integration of user-provided and third-party-developed analytical functions into the system's Library of Functions. Finally, user capability to customize a sequence of data operations by arbitrarily selecting functions from the Library of Functions and arranging them in any desired order so that the output of one function can serve as the input to a subsequent function is also provided by the system.

With those and other objects, advantages, and features of the invention that may become hereinafter apparent, the nature of the invention may be more clearly understood by reference to the following detailed description of the invention, the appended claims and to the several drawings attached herein.

DETAILED DESCRIPTION OF THE PREFERRED EMBODIMENT

Several preferred embodiments of the invention are described for illustrative purposes, it being understood that the invention may be embodied in other forms not specifically shown in the drawings.

Figure 1:
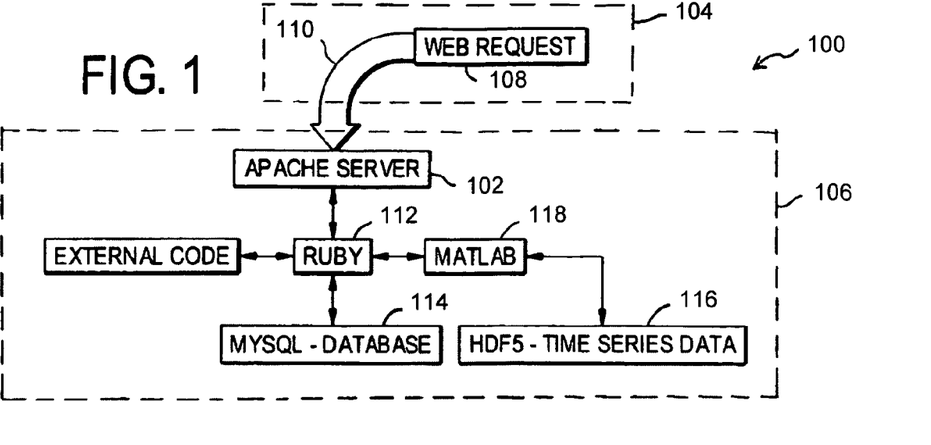
FIG. 1 is a block diagram showing one embodiment of the present invention.

Turning first to FIG. 1, shown therein is a block diagram of one embodiment of the present invention. The system 100 is a Web-based application and, therefore, uses a Web server to host it. In this case, an Apache server 102 is used for this purpose, but any hosting system and software could be used.

The invention consists of two basic parts: the client-side graphical user's interface (GUI) and client computer 104 and the server-side components 106. The GUI consists primarily of HTML/JavaScript files running on client computer 108. The user creates queries and function chains using the client GUI to provide input, via a network connection 110 for the analysis modules that reside entirely or mostly on the server 102, which will be described in more detail below.

The server side 106 is controlled by a Ruby component 112 that processes the user input parameters sent from the client computer 108 and stores them in various configuration files. On the server side, the queries are processed by Ruby, and function chains are processed by MATLAB®. MATLAB® is controlled by Ruby. Function chains require data to run. Thus, when MATLAB® is invoked, it is invoked with a subject ID and the name of the function chain. MATLAB® retrieves the time series data of the stated subject ID for the variable specified in the function chain from database 114. MATLAB® then runs the functions specified in the function chain, and returns the results to the client computer 108. Ruby then either displays the results to the user or uses the results to create an input file for the desired application.

Apache version 2 could be used for the invention. Apache secured socket layer (SSL) and Ruby modules are preferred. Apache accepts the incoming HTTP/S connection and invokes the appropriate entry point in Ruby depending on the requested URL. (If the URL contains a .rhtml, .rb, or .rbx, then Ruby code is invoked.) RHTML pages are codes written using 'eruby', a language that allows developers to embed Ruby scripts in HTML pages. In order to speed up the invocation of the embedded Ruby scripts, Apache uses a tool called 'mod_ruby' that embeds the Ruby interpreter into Apache, thereby allowing the scripts to be executed natively.

The Ruby code lies primarily in .rhtml files. Those files are processed to create the Web page. Ruby communicates with MATLAB® using the MATLAB® engine API. The engine Application programming interface (API) is accessed using C code. This C code is wrapped using SWIG that creates a Ruby interface. Ruby communicates with MySQL using the Ruby MySQL modules.

MATLAB® gets data from the HDF5 (binary) files using C code that invokes the HDF5 software libraries 116. This C code was compiled using the MATLAB® MEX compiler and is called as a MATLAB® function. MATLAB® just recently added their own HDF5 support.

The MySQL database 114 stores the system data as well as the non-time series experimental data. The system data consists primarily of user information. The MySQL database 114 preferably uses MySQL/Ruby. MySQL/Ruby is the MySQL API module for Ruby. It allows Ruby to talk to MySQL databases 114. The attribute data are stored in a MySQL database 114.

The time-series data is stored in HDF5, a high performance binary flat file that is optimized for array data storage.

The following Table I summarizes the components of the GUI software and server side components.

TABLE I

Description of the system modules

| Name | Description |
| --- | --- |
| Apache2 (with SSL) | HTTP server to receive requests, pass them to other modules and collect and send out results |
| Mod_ruby | Apache2 external module to pass Ruby scripts to Ruby language interpreter |
| Ruby | Ruby script language interpreter |
| eRruby | Ruby library to process Ruby script embedded in the html file |
| mysql_ruby | Ruby library to interface the MySQL database |
| Mysql | database engine to manage MySQL databases |
| SWIG | generating binary library as interface between two different language |
| HDF5 | Provide tools to generate HDF5 format data file to store huge time-series data and interface to access the data file |
| SVG | Image transfer and specifications |
| MATLAB ® | Provide application interface for accessing MATLAB ® functions |

This entire system could be implemented on a server running a Slackware 10.0 software distribution of Linux.

Figure 2:
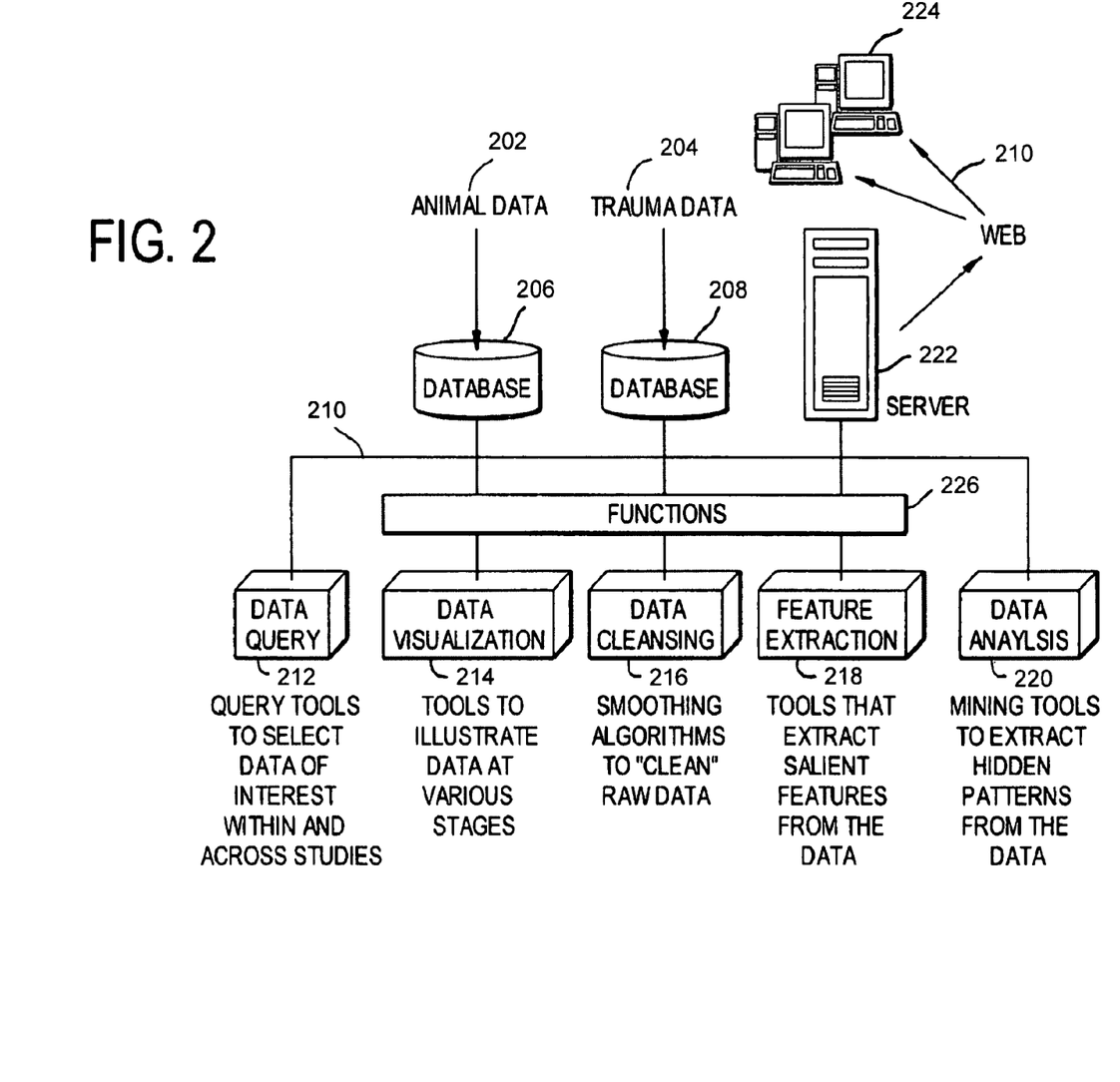
FIG. 2 is a schematic drawing illustrating various structures and functions of an embodiment of the present invention.

Turning now to FIG. 2, shown therein is a schematic drawing illustrating various structures and functions of the present invention, which will be described below.

Time-series data are collected from patients 202, 204 using, for example, a Propaq 206 vital signs monitor and recorded in a flash memory card or databases 206, 208 via a handheld computer (not shown). The Propaq continuously monitors several physiologic variables, including EKG, SpO2, respiratory rate, non-invasive blood pressure (NIBP), end-tidal CO2, and heart rate, with collection time ranging from 10-min to 30-min. Although physiological time-series data are used for illustrative purposes, it should be appreciated by artisans skilled in the art that the invention may be used on any time-series and non time-series data.

Each continuous physiologic variable in the data set is gathered at a different sampling frequency. Thus, over the same collection time period, the number of data points varies among each variable, presenting a challenge for analysis. The highest resolution variable, EKG waveform, is gathered at approximately 180.0 Hz, which results in approximately 324,000 data points for a 30-min data file acquisition. SpO2 and respiratory waveforms are gathered at approximately 91.0 Hz and 45.5 Hz, respectively. The lower frequency time-series data, including NIBP, end-tidal CO2, respiratory rate, and heart rate, are available at 1.0 Hz. However, new values of NIBP are only collected every 2.0-3.0 minutes, depending on the Propaq setting.

In addition to the Propaq vital sign data, other pertinent information, such as demographics data, cause and nature of injuries, LSI performed, and types and quantities of fluids delivered, are recorded and available for analysis.

Other time series data sets collected by other means are also contemplated to be within the nature and scope of the present invention. For example, nuclear and fossil power plants and chemical plants employ transducer and near and remote sensing devices coupled to data loggers for collecting systems information. Time-series data files can be archived from those data loggers for post-hoc analysis. Those same types of monitoring systems may also be used for monitoring critical systems, such as those on aircraft and the space shuttle. For example, the real-time monitoring of oxygen level and carbon dioxide levels and incident radiation aboard space flight vehicles may generate large data sets. In the financial industry, analysis of trends using large time-series data sets is of paramount importance to certain financial products and service providers.

Built on a combination of proven computational platforms and easily accessible through a data communications network 210, such as the Internet and the World Wide Web, the system and method of the present invention provide a flexible, modular, and interactive environment for prototyping and the incorporation of analytical tools. Facilities and tools provide for the storage of new studies and a query routine 212, visualize routine 214, cleanse routine 216, extract routine 218, and analyze physiologic data routine 220 with emphasis on tools to analyze time-series data. The system architecture provides both the data and the analysis tools that reside at a server 222, as shown in FIG. 2, while offering—through a Web browser on distributed client computers 224—a feature-rich, workstation-like environment that researchers require to perform sophisticated data mining. That architecture facilitates on-line collaboration among different research teams, allows for inter-study comparisons, and eliminates the need to download tools and data from the server 222 to the client computers 224, eliminating the often-painstaking process of installing the downloaded tools and managing the database records.

Users connect to the system using a standard Web browser and authenticate into their individual accounts by typing a user name and password. In order for the user to log into the system, the user presents the required credentials, username and password, and submits them. Those credentials are checked by looking at a user table inside a database, and if they are found to be valid, the system looks up the user's private directory. A session file is then created that contains the user's basic information from the user table, which consists of the user's private directory, the full name, whether they are able to import, and whether they are able to export. The initial session time is set to the system time at login.

The session file is used by the system to store temporary information during the course of the session. The timestamp on the session file is examined to see if it exceeds the logout threshold. If the difference between two requests, as measured by the current request time (system time) minus the previous request time (session time) is greater than that threshold, the session will time out, forcing the user to re-authenticate by presenting the user credentials in the login page. If the difference between requests is below the threshold, then the session time will be updated to equal the current system time. The interaction of the session file is contained inside the session object which is defined in the Ruby file: checksession.rb. Each request to the system is accompanied by a session key, a unique identifier that allows the system to know which session the request is associated with.

The system then goes to the users private directory and creates a list of all the "workspaces" assigned to that user, by looking at the file folders in the user's "wks" directory. Inside each of the relevant user directories is a file named wksname.txt That file contains the name of the workspace. In those directories, there may exist a file named deleted.txt. If that file is present, then the workspace is skipped. Once all of the valid workspaces are determined, the user is then presented with the page to select an existing workspace, create a new workspace, or delete a workspace.

If the workspace is deleted, then a deleted.txt file will be created inside that workspace folder, and the page will be redisplayed without that workspace as an option.

If a new analysis is created, then a directory will be created inside the user's "/wks" folder, and the name of the workspace will be placed in the wksname.txt folder. If an analysis is created or an existing analysis is selected, the active workspace will be set, inside the session file, to be that workspace.

Inside the system, user interaction is segmented into three distinct components as shown in FIG. 2: Query 212, Functions 226, and Analysis 220. Albeit separate and independently customized by the user, those components are integrated by an automatic tracking system that keeps track of the sequence of operations performed in a given session. Those operations can be saved and stored in the server 222 for future use. The three components are easily applied through pull down menus designed to permit the construction of arbitrary sequence of operations that analysts perform during data mining. The system allows researchers to transition away from the mundane yet necessary task of data and system management and focus on data mining and analysis.

During the Query phase using the Query routines 212, the researcher selects a subset of subjects from the study. Once those subjects have been identified, they are recorded within the system for use during Analysis.

In terms of the GUI, a navigation bar provides the four basic choices Query Data, Manage Functions, Analyze Data, and Exit. The choices for Export Data and Import Data will only be available if they are set to "on" (i.e., 1) in the session file. The Query page is rendered by the Ruby program managequeries.rhtml. The displayed form itself is powered by javascript code. There are three parts to the form. There is the information that governs how the forms work and manages query creation, deletion, and modification. There is the information regarding the data in the experiment. And lastly, there is the information which defines the query itself, which is built using the data in the experiment according the rules of query construction. The first two segments of code are the same for all users, and the last piece is specific to each user. The form information is described in the file query.js; the experiment info lies in querycatalogs.js; and the query info javascript file is in the user directory: queries.js.

Using that form, the user creates, modifies or deletes queries. Once they are finished, the user selects the Run button to save the data. When the Run button is selected, the form data is processed by the Ruby program parsequery.rhtml. That file saves the name of each query into a querylist. The querylist is maintained in a file querylist.txt, which is located in the directory of the workspace. The final step that is done once the queries are created is the creation of a javascript file which defines the existing queries for use by the form. That file is called queries.js and resides in the user's directory.

To actually run the query, a function in the Ruby program query.rb is run with the name of the query. The key difference between the various functions that are run in query.rb is the output of the functions.

Turning now to the Function phase of the system, analytical functions 226—in the form of data visualization routines 214, data cleansing routines 216, and feature extraction routines 218—available through a library of functions 226 within the system, are assembled by the researcher to operate on variables present within the study. Any library function may be applied to any variable in any order, subject to function constraints.

In the Analysis phase using Analysis routines 220, the efforts of the previous two phases are married. The functions are applied to the subjects harvested by the queries, and the results are fed into additional mining tools for more involved analysis, such as feature selection and classification algorithms.

In terms of the GUI, the Analyze Data link is primarily used to invoke an application across the population defined in a query, using the output data from selected function chains. Analysis is invoked simply by calling the analyse.rhtml code which generates a list of choices for analysis. Depending on the choice selected, the system will run the appropriate program. The programs in turn use the same mechanics to run queries and function chains as described in the previous sections. The only key difference is the handling of the output. Once the function chain data are processed for a given subject, they are formatted and placed into the input of the analysis component which could be any third party application.

The following is a list of files applicable to the operation of the system:
  pdb.rb: has many of the constants used
  checksession.rb: tracks session information
  convert2js.rb: creates javascript code for queries and function chains
  createwks.rb: creates a new workspace
  query.rb: runs queries
  DOM.js: contains helper code for DOM object construction in javascript
  initcatalogs.js: contains definitions for functions
  managefunctions.js: gui for management of function form
  querycatalogs.js: contains definitions of query variables
  query.js: gui for management of query form
  login.rhtml: logs user into the system
  managefunctions.rhtml: creates form for manage functions
  analyse.rhtml: creates form for analyse
  managequeries.rhtml: creates form for manage queries
  master.rhtml: lays out main page
  header.rhtml: lays out header
  nav.rhtml: lays out navigation section of page
  parsequery.rhtml: parses query information
  parsevars.rhtml: parses function information
  run_function_chain.m: runs the function chain
  read_function_chain.m: reads the function chain
  get_function_chain_data.m: loads time series variable data, uses readHDF5set
  readHDF5set.mexglx: MATLAB® function to access HDF5 data
  run_function_link.m: runs a function inside the function chain
  mygraph.m: graphs a function
  viewgraph.m: creates a custom graph specific to the output of the function
  matlab.so: gateway library used by Ruby to access MATLAB® externally.

Users construct queries by selecting variables from the list of potential choices within the study and limiting the ranges of the variables by selecting the corresponding constraints using the GUI interface. Once the list of constraints is created, the users run the query and the system returns a list of subjects that meet the selected constraints. For example, a query (termed "females, age 30-40, intubated") may return a list of female patients between ages 30-40 which had a pre-hospital intubation LSI. From that list, each subject can be selected for viewing in greater detail. The system records all the information related to a query, including any selected sub list, as a named object within the system, allowing the researcher to track exactly what constitutes the outcome of a particular query.

During the Function phase, the researcher selects variables upon which to perform analysis. First, a variable from within the study is chosen. Then, individual functions are selected in sequence from a library of functions to construct a function chain, which defines the order of the mathematical operations to be applied to the chosen variable. Those functions allow for data visualization, data cleansing, and feature extraction, spanning a variety of tools, such as data zooming, wavelet transform for noise filtering, and mathematical and statistical functions like minimum, maximum, standard deviation, and trending for feature extraction. The system allows for easy and rapid integration of user-provided and third-party-developed analytical functions into the system's library of functions. Functions can be written in C, FORTRAN, Java®, or MATLAB®, allowing algorithms to be provided by various research teams.

Function chains permit the user to customize a sequence of data operations by selecting functions from the library of functions and arranging them in any desired order so that the output of one function can serve as the input to a subsequent function. Built-in mechanisms automatically construct function input-output interfaces and check for function-to-function consistency. Another advantage of function chains is that they only instantiate the functions in the sequence and generate derivative data when requested by the user, reducing the amount of data the system has to manage. Once those functions are completed, they are saved as named objects within the system and accessible for later use.

For example, the "EKG function chain" is constructed to identify the peaks and compute the R-R interval distance for a small range of an EKG trace. That is done by selecting the "EKG Waveform" variable type, and subsequently selecting two functions: "Range Selection" and "RR Interval." If the researcher desires to instantiate the function and see its output in graphical or numerical format at any point along the function chain, the researcher can simply click on the link associated with that function. For instance, the graphical visualization of the R-R interval is constructed by clicking on a "Graph" button associate with the "RR Interval" function. If the researcher wishes to compute the standard deviation of the distances among the peaks, he/she simply selects the standard deviation function from the "Select Function To Add" pull down menu, click the "Add Function" button, and the standard deviation function is placed at the tail of the function chain to create the "EKG function chain."

The Analysis component 220 allows the user to apply a desired set of function chains to any subset of the query results. For example, Table II shows the results of running an "EKG function chain" against the subjects from a query "females, age 30-40, intubated." This allows users to easily apply functions across a group of subjects in an interactive manner, permitting function chains and queries to be modified and fine tuned, leaving the system to track the mechanisms being used to produce the analysis.

TABLE II

Results of query.

| Subject ID | Standard Deviation of R-R Interval (ms) |
|---|---|
| 67 | 2.9 |
| 94 | 72.2 |
| 96 | 208.6 |
| 107 | 3.2 |
| 110 | 26.6 |
| 127 | 2.4 |
| 130 | 279.5 |
| 398 | 162.7 |
| 518 | 519.2 |

The Analysis component 220 also hosts algorithms for in-depth multivariate data mining. Tools to collect the feature variables resulting from the application for function chains to queries and to concatenate such features into input files for subsequent application of feature selection and classification algorithms are also contemplated. Feature selection algorithms, such as linear correlation coefficients and information entropy, and classification algorithms, such as artificial neural networks, decision trees, and support vector machines, are integrated into the system for sophisticated data mining.

The system emphasizes performance, modularity, flexibility, and third-party software integration. In the Query component 212, the system can assess "provide the subjects/data for which there are at least 5 minutes of uninterrupted EKG data within 20 minutes of the incident." Another salient query feature is cross-study query. In the scope of the Function 226 and Analysis 220 components, the functions can be added directly by the user without the need for an engineer to manually add third-party algorithms. That allows the system to satisfy the research needs of a sophisticated and diverse user population. Also, more interactive visualization tools are contemplated to allow graphical exploration of time-series data in time and frequency domain.

Figure 3:
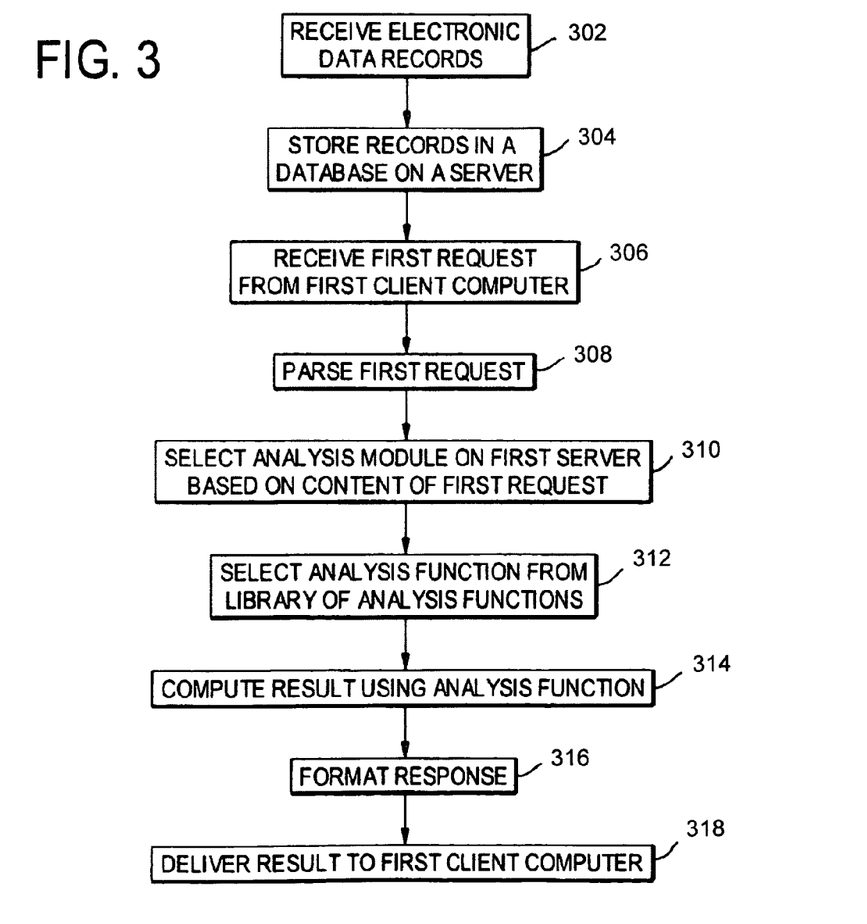
FIG. 3 is a process flow diagram illustrating the method of using the present invention.

Turning now to FIG. 3, shown therein is a process flow diagram illustrating the method of using the present invention in more of a simplified overview. The system requires that clients have Internet access and a Web-browser; all data storage, access, analysis, and graphics functions reside on a server as noted previously. Besides Query and Analysis functions 212, 220 (see FIG. 2), the client/user can visualize the attributes and time-series data, output results in reports, export the results or raw data as files, and share data and analytic routines amongst other users.

The basic steps involved in using the invention include, as shown in step 302, first receiving, over a communications network, a set of electronic data records. Those records may be in any format initially, and may be time-series data or non time-series data. It is anticipated that most of the data files will be bundled and formatted for transfer over a conventional packet-switched network, such as the Internet, using a conventional transfer protocol (i.e., Internet Protocol). The data records may also be downloaded using a direct link to a monitoring device or that device's data logger as discussed previously (see FIG. 2).

In step 304, the electronic data records are stored in at least one database that is associated with a host server. Multiple databases may be used. The server may be a single server or multiple, networked servers in different locations.

In step 306, the server receives a first request from a first client computer and in step 308 parses the first request to extract the query tools, analysis tool (from a library of analysis tools available), and other information needed to execute operations in the Query 212, Function 226, and Analysis 220 component routines and to return information to the client computers 224 (as best seen in FIG. 2).

In step 310, an analysis module stored on the first server is selected based on the content of the first request, and in step 312 and analysis function from a library of functions is selected. Each function can be sequentially executed as a function chain. The chain accomplishes two objectives: 1) the selection (i.e., query), based on client supplied constraints applied to attribute and/or time-series data, of a subset of subjects from the database, and 2) the mathematical analysis of time-series data associated with each of the selected subjects. The function chain architecture, because of its inherent modularity, allows substantial flexibility in performing query and analysis of attribute and time-series data. The client/user can perform standard database queries on attribute data, but also can directly query a) the original time-series data, or b) the results after application of analytical procedures to the time-series data.

Some of the library of functions include functions that are applied exclusively to attribute data and always select subjects that meet user supplied constraints (i.e., they produce a reduced set of subjects while the variable remains unchanged). Examples of such functions are ones that select subjects based on gender, or that select patients based on whether they received more than 1 unit of blood in a hospital.

Other available functions include those that always mathematically manipulate scalar or time-series data to generate new time-series data or a scalar result. These functions only change the data; the set of subjects remains the same. An example of such a function is one that extracts a specified range of data from time series files. In this case, a new time series that is smaller than the original is generated for each subject.

Still, other functions include those that always mathematically manipulate scalar or time-series data to generate new time-series data or a scalar result as described above; in addition, if the user applies constraint criteria to the output of the function, the function also selects a subset of subjects. This type of function changes both the data and the set of subjects. For example, this kind of function can calculate the length of all time-series data files for each subject in a set of subjects, in which case only the output data, but not the number of subjects, is changed. However, if the user specifies a length constraint, then the output from this step will be the time-series file lengths only for the subjects that meet the length constraint (i.e., both the data and the set of subjects are changed).

In step 314, the function is applied to the data records in the database to produce a useful result. In step 316, the system formats a response to the initial query using at least the result from the analysis function from step 314. In step 318, the system delivers (i.e., pushes the information down to the client) or provides (i.e., makes the information available to be pulled by the client) the result to the first client computer. The information is made available via the client computer browser, which makes it easy to select and view all time series data in the database, including original and new time-series data calculated by the individual and chain functions. The primary output page displayed on the client computer results from the execution of the function chain and is similar to a spreadsheet in which each subject is a row, and variables are columns. The results include the selected subset of subject ID's, the subjects' attribute or scalar data, and links to associated time-series data. Three other pages can be opened from the report page to provide additional, specialized views of the results.

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

We claim:

1. A computer network including a computer-implemented data evaluation tool for evaluating electronic data sets and capable of displaying an output of the evaluation on a display medium, comprising:

a communications network;

a first server in data communication with the communications network;

a first electronic database stored on the first server and populated with data records in a plurality of record series, the data records including a plurality of attribute data records containing data fields populated with discrete information and at least a plurality of time-series of data records containing data fields populated with time-series information;

a plurality of analysis modules on the first server, each of the plurality of analysis modules adapted to input a set of client-customized operations to the record series in the database and output results that satisfy the operations, the analysis modules providing mathematical manipulation of attribute and/or time-series data to generate new time-series data or a scalar result, the mathematical manipulation comprising at least one mathematical manipulation that integrates two or more of the record series, the analysis modules comprising a data query module capable of querying across different studies in the database and retrieve specific data subsets that meet client-defined criteria, and the analysis modules comprising a data analysis module having an ability to perform mathematical manipulations of the attribute and/or time-series data on the data subsets satisfying the query results;

a data analysis customizing function, permitting the client to customize in an interactive, arbitrary manner the data query module and the data analysis module by selecting study data from the database and analysis function operators from a library of functions and arranging them in a desired, sequential order, wherein the analysis function operators perform mathematical manipulations on the study data for generating the result;

at least one of said analysis customization, utilizing the data query module, wherein the client customizes the query using at least one of the study data from the database and a plurality of analysis function operators from the library of functions sequentially arranging the data and the functions as a function chain, so that the output of one function serves as the input to a subsequent function, the function chain effecting a selection based on client-supplied constraints applied to attribute and/or time-series data, resulting in the retrieval of data subsets that satisfy client query customization intent;

at least one of said analysis customization functions utilizing the data analysis module, wherein the client customizes analysis using at least one of the study data from the database and a plurality of analysis function operators from the library of functions sequentially arranging the data and the functions as a function chain, so that the output of one function serves as the input to a subsequent function, the function chain operating on the data subsets retrieved by the query module and using client-supplied constraints to perform mathematical operations to attribute and/or time-series data, resulting in derivative scalar and/or time-series data that satisfy client analysis customization intent applied to results of query module; and a first interface associated with a first client computer in data communication with the communications network, the first interface adapted to sending a request to one of the plurality of analysis modules and adapted to displaying on the first client computer the result.

2. The data evaluation tool according to claim 1, wherein the first interface has a capability of selectively displaying at least some of the time-series data records or said result after application of analytical procedures to the time-series data.

3. The data evaluation tool according to claim 2, wherein the time-series data records one of EKG, SpO2, respiratory rate, NIBP, end-tidal CO2, and heart rate time-series data.

4. The data evaluation tool according to claim 1, wherein the plurality of analysis modules comprises at least one of a data visualization module and data cleansing module.

5. The data evaluation tool according to claim 1, further comprising:

a second interface associated with a second client computer in data communication with the communications network, the second interface adapted to sending a request to one of the plurality of analysis modules and displaying on the second client computer the result, thereby eliminating a need to download tools and data from the first server to the client computers;

the data evaluation tool providing an architecture that facilitates on-line collaboration among different users, allows for inter-study comparisons; and the data evaluation tool further managing the database records.

6. The data evaluation tool according to claim 1, further comprising a library of data analysis functions stored on the first server, wherein each of the analysis functions comprises an analysis function operator for generating the result.

7. The data evaluation tool according to claim 6, comprising providing the analysis function operator as a univariate or multivariate data operator.

8. The data evaluation tool according to claim 1, further comprising a second database stored on the first server and populated with data records, wherein the records in the first database differ from the records in the second database, thereby permitting multiple databases to generate the new time-series data or scalar result.

9. The data evaluation tool according to claim 1, further comprising the analysis module receiving plural data sets, at least one of said data sets includes data gathered at a different sampling frequency and having a different number of data points from another one of said data sets, thereby permitting multiple databases to generate the new time-series data or scalar result.

10. The data evaluation tool according to claim 9, further comprising the analysis modules obtaining further data comprising the source of the data sets, said further data used to analyze the data sets.

11. The data evaluation tool according to claim 1, further comprising:

a library of data analysis functions stored on the first server, wherein each of the analysis functions comprises an analysis function operator for generating the result;

at least one of said analysis functions stored on the first server selected based on the content of the request providing an analysis function from the library of data analysis functions, and in the case of plural functions, sequentially executing the functions as a function chain, the function chain effecting a selection based on client supplied constraints applied to attribute and/or time-series data, of a subset of subjects from the database, and effecting a mathematical analysis of time-series data associated with each of the selected subjects.

12. The data evaluation tool according to claim 1, further comprising:

the data analysis customizing function comprising a library of data analysis functions stored on the first server, wherein each of the analysis functions comprises an analysis function operator for generating the result;

at least one of said analysis functions stored on the first server selected based on the content of the request providing an analysis function from the library of data analysis functions, and in the case of plural functions, sequentially executing the functions as a function chain, the function chain effecting a selection based on client supplied constraints applied to attribute and/or time-series data, of a subset of subjects from the database, and effecting a mathematical analysis of time-series data associated with each of the selected subjects, the analysis selectively comprising standard database queries on attribute data, and capable of selecting one of directly query based on the original time-series data, or results after application of analytical procedures to the time-series data.

13. The data evaluation tool according to claim 1, further comprising:

the data analysis customizing function comprising a library of data analysis functions stored on the first server, wherein each of the analysis functions comprises an analysis function operator for generating the result; and at least one of the analysis modules able implement individual functions are selected in sequence from a library of functions in a function chain to permit the user to customize a sequence of data operations by selecting functions from the library of functions and arrange the functions in a desired order.

14. A communications network-enabled tool for evaluating electronic data sets in a distributed computing environment, comprising:

a server;

an electronic database in data communications with the server and populated with data records in a plurality of record series, the data records including a plurality of attribute data records containing data fields populated with discrete information and at least a plurality of time-series of data records containing data fields populated with time-series information;

a plurality of analysis modules associated with the server and adapted to input a set of client-customized operations to the record series in the database and output results that satisfy the operations, the analysis modules providing mathematical manipulation of attribute and/or time-series data to generate new time-series data or a scalar result, the mathematical manipulation comprising at least one mathematical manipulation that integrates two or more of the record series, the analysis modules comprising a data query module capable of querying across different studies in the database and retrieve specific data subsets that meet client-defined criteria, and the analysis modules comprising a data analysis module having an ability to perform mathematical manipulations of the attribute and/or time-series data on the data subsets satisfying the query results;

a data analysis customizing function, permitting the client to customize in an interactive, arbitrary manner the data query module and the data analysis module by selecting study data from the database and analysis function operators from a library of functions and arranging them in a desired, sequential order, wherein the analysis function operators perform mathematical manipulations on the study data for generating the result;

at least one of said analysis customization functions utilizing the data query module, wherein the client customizes the query using at least one of the study data from the database and a plurality of analysis function operators from the library of functions sequentially arranging the data and the functions as a function chain, so that the output of one function serves as the input to a subsequent function, the function chain effecting a selection based on client-supplied constraints applied to attribute and/or time-series data, resulting in the retrieval of data subsets that satisfy client query customization intent;

at least one of said analysis customization, utilizing the data analysis module, wherein the client customizes analysis using at least one of the study data from the database and a plurality of analysis function operators from the library of functions sequentially arranging the data and the functions as a function chain, so that the output of one function serves as the input to a subsequent function, the function chain operating on the data subsets retrieved by the query module and using client-supplied constraints to perform mathematical operations to attribute and/or time-series data, resulting in derivative scalar and/or time-series data that satisfy client analysis customization intent applied to results of query module;

a plurality of client computers in data communication with the server adapted to sending a request to one of the plurality of analysis modules; and an interface associated with each of the plurality client computers for displaying the result on at least one of the plurality of client computers.

15. The evaluation tool according to claim 14, wherein:

the parameters of the predetermined class provide early indicators of a clinical outcome; and the data records are time-series data records containing data fields populated with physiological time-series information.

16. The evaluation tool according to claim 14, wherein the plurality of analysis modules comprises at least one of a data visualization module and data cleansing module.

17. The evaluation tool according to claim 14, further comprising a library of data analysis functions stored on the server, wherein each of the analysis functions comprises an analysis function operator for generating the result.

18. The evaluation tool according to claim 14, further comprising the analysis module receiving plural data sets, at least one of said data sets includes data gathered at a different sampling frequency and having a different number of data points from another one of said data sets, thereby permitting multiple databases to generate the new time-series data or scalar result.

19. The evaluation tool according to claim 18, further comprising the analysis modules obtaining further data related to the source of the data sets, said further data used to analyze the data sets.

20. The evaluation tool according to claim 14, further comprising:

a library of data analysis functions stored on the first server, wherein each of the analysis functions comprises an analysis function operator for generating the result;

at least one of said analysis functions stored on the first server selected based on the content of the request providing an analysis function from the library of data analysis functions, and in the case of plural functions, sequentially executing the functions as a function chain, the function chain effecting a selection based on client supplied constraints applied to attribute and/or time-series data, of a subset of subjects from the database, and effecting a mathematical analysis of time-series data associated with each of the selected subjects.

21. The evaluation tool according to claim 14, further comprising:

the data analysis customizing function comprising a library of data analysis functions stored on the first server, wherein each of the analysis functions comprises an analysis function operator for generating the result;

at least one of said analysis functions stored on the first server selected based on the content of the request providing an analysis function from the library of data analysis functions, and in the case of plural functions, sequentially executing the functions as a function chain, the function chain effecting a selection based on client supplied constraints applied to attribute and/or time-series data, of a subset of subjects from the database, and effecting a mathematical analysis of time-series data associated with each of the selected subjects, the analysis selectively comprising standard database queries on attribute data, and capable of selecting one of directly query based on the original time-series data, or results after application of analytical procedures to the time-series data.

22. The evaluation tool according to claim 14, further comprising:

the data analysis customizing function comprising a library of data analysis functions stored on the first server, wherein each of the analysis functions comprises an analysis function operator for generating the result; and at least one of the analysis modules able implement individual functions are selected in sequence from a library of functions in a function chain to permit the user to customize a sequence of data operations by selecting functions from the library of functions and arrange the functions in a desired order.

23. A method for evaluating electronic data records over an electronic communications network, comprising the steps of:

receiving over a communications network a set of electronic data records;

storing the set of electronic data records in a plurality of record series in at least one database on a server, the data records including a plurality of attribute data records containing data fields populated with discrete information and at least a plurality of time-series of data records containing data fields populated with time-series information;

receiving at the server a first instruction from a remote client computer to identify one or more of the data records, the data records including time-series data records containing data fields populated with time-series information;

receiving at the server a second instruction to input a set of client-customized operations to be applied to the identified data records;

receiving at the server a third instruction to analyze the result of the applied mathematical operation, the analysis providing mathematical manipulation of attribute and/or time-series data to generate new time-series data or a scalar result;

formatting a response using at least the result from the applied mathematical operation and output results that satisfy the operations, the parameters providing early indicators of an evaluation outcome, the analysis allowing query across different studies in the database and retrieve specific data subsets that meet client-defined criteria, and the analysis able to perform mathematical manipulations of the attribute and/or time-series data on the data subsets satisfying the query results;

permitting the client to customize in an interactive, arbitrary manner a data query module and a data analysis module by selecting study data from the database and analysis function operators from a library of functions and arranging them in a desired, sequential order, wherein the analysis function operators perform mathematical manipulations on the study data for generating the result;

customizing the query using at least one of the study data from the database and a plurality of analysis function operators from the library of functions sequentially arranging the data and the functions as a function chain, so that the output of one function serves as the input to a subsequent function, the function chain effecting a selection based on client-supplied constraints applied to attribute and/or time-series data, resulting in the retrieval of data subsets that satisfy client query customization intent;

customizing analysis using at least one of the study data from the database and a plurality of analysis function operators from the library of functions sequentially arranging the data and the functions as a function chain, so that the output of one function serves as the input to a subsequent function, the function chain operating on the data subsets retrieved by the query and using client-supplied constraints to perform mathematical operations to attribute and/or time-series data, resulting in derivative scalar and/or time-series data that satisfy client analysis customization intent applied to results of query module; and delivering or providing the result to the client computer, wherein the first, second, and third instructions are part of the same request or a different request.

24. The method according to claim 23, further comprising selectively displaying at least a portion of a time-series data set or the result after application of analytical procedures to the time-series data.

25. The method according to claim 24, wherein:

the parameters of the predetermined class provide early indicators of a clinical outcome; and the time-series data set is a physiologic time-series data set.

26. The method according to claim 23, wherein the step of receiving a set of electronic data records comprises collecting electronic signals from a monitoring device.

27. The method according to claim 23, wherein the steps of receiving the instructions and delivering or providing the result are done over a secure HTTP connection between the server and the client computer, thereby facilitating on-line collaboration among different users and eliminating a need to download tools and data from the first server to the client computers.

28. The method according to claim 23, further comprising the step of:

receiving authentication information from a user; and comparing the authentication information to credentials stored in the at least one database.

29. The method according to claim 23, further comprising the step of:

receiving a plurality of instructions from the remote client computer; and outputting a customized analysis report.

30. A method for mining and analyzing electronic data records over a distributed network of client computers, comprising the steps of:

storing on a central server a set of data records obtained from an electronic monitoring device in a plurality of record series;

receiving a data mining request, a function request, and an analysis request from a remote client computer;

selecting a subset of the data records based on the data mining request, the data records including a plurality of attribute data records containing data fields populated with discrete information and at least one a plurality of time-series data records containing data fields populated with time-series information;

performing at least one mathematical operation on the subset of data records based on the function request;

performing an analysis of a result of the at least one mathematical operation based on the analysis request by identifying parameters of a predetermined class, the analysis providing mathematical manipulation of scalar or time-series data to generate new time-series data or a scalar result, the parameters providing early indicators of an evaluation outcome, the mathematical manipulation comprising at least one mathematical manipulation that integrates two or more of the record series, the analysis allowing query across different studies in a database and retrieve specific data subsets that meet client-defined criteria, and the analysis able to perform mathematical manipulations of the attribute and/or time-series data on the data subsets satisfying the query results;

a data analysis customizing function, permitting the client to customize in an interactive, arbitrary manner a data query module and a data analysis module by selecting study data from the database and analysis function operators from a library of functions and arranging them in a desired, sequential order, wherein the analysis function operators perform mathematical manipulations on the study data for generating the result;

customizing the query using at least one of the study data from the database and a plurality of analysis function operators from the library of functions sequentially arranging the data and the functions as a function chain, so that the output of one function serves as the input to a subsequent function, the function chain effecting a selection based on client-supplied constraints applied to attribute and/or time-series data, resulting in the retrieval of data subsets that satisfy client query customization intent;

customizing analysis using at least one of the study data from the database and a plurality of analysis function operators from the library of functions sequentially arranging the data and the functions as a function chain, so that the output of one function serves as the input to a subsequent function, the function chain operating on the data subsets retrieved by the query and using client-supplied constraints to perform mathematical operations to attribute and/or time-series data, resulting in derivative scalar and/or time-series data that satisfy client analysis customization intent applied to results of query module; and delivering or providing a response to the client computer containing information about the subset of data records, the result of the at least one mathematical operation, and the analysis of the result.

31. The method for mining and analyzing electronic data records according to claim 30, wherein:
the parameters of the predetermined class provide early indicators of a clinical outcome; and
the subset of data records includes physiologic time-series data.

32. The method for mining and analyzing electronic data records according to claim 30, wherein the steps of receiving, selecting and performing are done by the central server.

33. The method for mining and analyzing electronic data records according to claim 30, further comprising the receiving plural data sets, at least one of said data sets includes data gathered at a different sampling frequency and having a different number of data points from another one of said data sets, thereby permitting multiple databases to generate the new time-series data or scalar result.

34. The method for mining and analyzing electronic data records according to claim 33, further comprising obtaining further data related to the source of the data sets to analyze the data sets.

35. The method for mining and analyzing electronic data records according to claim 30, further comprising:
storing a library of data analysis functions stored on the central server, wherein each of the analysis functions comprises an analysis function operator for generating the result;
providing an analysis based on the content of the request from the library of data analysis functions, and in the case of plural functions, sequentially executing the functions as a function chain, the function chain effecting a selection based on client supplied constraints applied to attribute and/or time-series data, of a subset of subjects from the database, and effecting a mathematical analysis of time-series data associated with each of the selected subjects.

36. The method for mining and analyzing electronic data records according to claim 30, further comprising:
the execution of the data analysis customizing function comprising storing a library of data analysis functions stored on the central server, wherein each of the analysis functions comprises an analysis function operator for generating the result;
providing an analysis based on the content of the request from the library of data analysis functions, and in the case of plural functions, sequentially executing the functions as a function chain, the function chain effecting a selection based on client supplied constraints applied to attribute and/or time-series data, of a subset of subjects from the database, and effecting a mathematical analysis of time-series data associated with each of the selected subjects, the analysis selectively comprising standard database queries on attribute data, and capable of selecting one of directly query based on the original time-series data, or results after application of analytical procedures to the time-series data.

37. The method for mining and analyzing electronic data records according to claim 30, further comprising:
the execution of the data analysis customizing function comprising storing data analysis functions as a library, wherein each of the analysis functions comprises an analysis function operator for generating the result; and
at least one of the analysis modules able implement individual functions are selected in sequence from a library of functions in a function chain to permit the user to customize a sequence of data operations by selecting functions from the library of functions and arrange the functions in a desired order.

* * * * *

UNITED STATES PATENT AND TRADEMARK OFFICE
CERTIFICATE OF CORRECTION

PATENT NO. : 7,779,025 B2
APPLICATION NO. : 11/298606
DATED : August 17, 2010
INVENTOR(S) : Jamila Gunawardena et al.

It is certified that error appears in the above-identified patent and that said Letters Patent is hereby corrected as shown below:

On the Title page:

Please delete:
Item "(75) Inventors: Jamila Gunawardena, Palo Alto, CA (US); Jacques Reifman, New Market, MD (US)"

and replace with:
Item -- (75) Inventors: Jamila Gunawardena, Palo Alto, CA (US); Jaques Reifman, New Market, MD (US) --

Signed and Sealed this

Nineteenth Day of October, 2010

David J. Kappos
*Director of the United States Patent and Trademark Office*